(12) United States Patent
Lee et al.

(10) Patent No.: US 10,584,153 B2
(45) Date of Patent: Mar. 10, 2020

(54) TREATMENT OF DAMAGED NERVE WITH PTEN INHIBITOR

(71) Applicant: TISSUEGENE, INC., Rockville, MD (US)

(72) Inventors: Kwan Hee Lee, Rockville, MD (US); Moon Jong Noh, Rockville, MD (US); Kwangwook Ahn, Rockville, MD (US)

(73) Assignee: Kolon TissueGene, Inc., Rockville, MD (US)

( * ) Notice: Subject to any disclaimer, the term of this patent is extended or adjusted under 35 U.S.C. 154(b) by 0 days.

(21) Appl. No.: 15/142,324

(22) Filed: Apr. 29, 2016

(65) Prior Publication Data

US 2016/0340396 A1 Nov. 24, 2016

Related U.S. Application Data

(63) Continuation of application No. PCT/US2014/063900, filed on Nov. 4, 2014.

(60) Provisional application No. 61/899,795, filed on Nov. 4, 2013.

(51) Int. Cl.
  *C07K 14/47* (2006.01)
  *C12N 9/16* (2006.01)
  *A61K 38/00* (2006.01)

(52) U.S. Cl.
  CPC ............ *C07K 14/4703* (2013.01); *C12N 9/16* (2013.01); *C12Y 301/03067* (2013.01); *A61K 38/00* (2013.01)

(58) Field of Classification Search
  None
  See application file for complete search history.

(56) References Cited

U.S. PATENT DOCUMENTS

2009/0305333 A1* 12/2009 He .................. A61K 31/28
                                                 435/29
2012/0107299 A1    5/2012 Morishita et al.
2012/0269829 A1* 10/2012 Wang ................. A61K 9/0019
                                                 424/178.1

FOREIGN PATENT DOCUMENTS

WO      2013067125 A1    5/2013

OTHER PUBLICATIONS

Ohtake 2015 "PTEN inhibition and axon regeneration and neural repair" Neural regen Res 10(9):1363-1368.*
Rahdar 2009 "A phosphorylation-dependent intramolecular interaction regulates the membrane association and activity of the tumor suppressor PTEN" PNAS 106(2):480-485.*
Song 2012 "the functions and regulations of the PTEN tumor suppressor" nature reviews 13:283-296Tor.*
Torres 2001 "the tumor suppressor pten is phosphorylated by the protein kinase CK2 at its c terminus" JBC 276(2):993-998.*
International Search Report and Written Opinion from PCT/US14/063900, dated Mar. 10, 2015.
Vazquez et al., "Phosphorylation of the PTEN tail acts as an inhibitory switch by preventing its recruitment into a protein complex," J. Biol Chem., Nov. 13, 2001, vol. 276, pp. 48627-48630.

* cited by examiner

*Primary Examiner* — Adam Weidner
(74) *Attorney, Agent, or Firm* — Nixon & Vanderhye P.C.

(57) ABSTRACT

The present application discloses a method of growing or proliferating nerve cells by contacting the cells with phosphatase and tensin homolog (PTEN) lipid phosphatase inhibiting peptide.

10 Claims, 5 Drawing Sheets

Specification includes a Sequence Listing.

* TGN-1 Peptide : RRRRRRRR-VTPDV(pS)DNEPDHYRY(pS)DTTD(pS)DPE-amide
* TGN-2 Peptide : RRRRRRRR-HYRY(pS)DTTD(pS)DPENEPFDEDQHTQITKV-amide
* TGN-3 Peptide : RRRRRRRR-HYRYVDTTDVDPENEPFDEDQHTQITKV-amide
* TGN-4 Peptide : RRRRRRRR-SDDEYTDNPDSRYVSDTPVDTEH-amide → TGN-1 scrambled sequence
* TGN-5 Peptide : RRRRRRRR-DEHDTEYTPDYRQETHPNSQPTDKSDVI-amide → TGN-2,3 scrambled sequence 1: PC12 cell lysate : w/TGN-1 (10 µM)
2: PC12 cell lysate : w/TGN-4 (10 µM)
3: PC12 cell lysate : w/TGN-1 (100 µM)
4: PC12 cell lysate : w/DMSO (2 µL)

1: PTEN transfection + TGN-1
2: PTEN transfection + TGN-4
3: TGN-1 only
4: TGN-4 only

TREATMENT OF DAMAGED NERVE WITH PTEN INHIBITOR

BACKGROUND OF THE INVENTION

1. Field of the Invention

The present application relates to a method of regenerating nerve or attenuating degeneration of injured nerve by administering at or an area near an injured nerve, a nerve regenerating or nerve degeneration attenuating amount of phosphatase and tensin homolog (PTEN) lipid phosphatase inhibiting peptide.

2. General Background and State of the Art

In adult mammalian nervous system, regeneration of damaged neurons hardly occurs in healing response to nerve injury. There are two main reasons why adult CNS neurons fail to regenerate after injury—axons do not regenerate in adult central nervous system not only because of its inhibition by secreted extracellular inhibitory factors upon injury, but also because of the loss of intrinsic axon growth ability, which rapidly declines through aging [Schwab et al; 1996, Goldberg et al. 2002; Filbin et al. 2006; Fitch et. al 2008]. However, elimination of extracellular inhibitory molecules secreted upon nerve injury only triggers very limited axon regeneration in vivo [Yiu et. al 2006; Hellal et al. 2011]. Thus, promoting axonal regeneration process by regulation of intrinsic nerve outgrowth is currently focus of a therapeutic target for nerve injury treatment.

PTEN (phosphatase and tensin homolog) protein is a dual phosphatase and is considered to be important as tumor suppressor by negatively regulating phosphatidylinositol3-kinase (PI3K) signaling pathway. The PI3K signaling pathway is a critical signal transduction pathway for cell proliferation, survival and differentiation as well as protein synthesis, metabolism and motility [Zhang et al. 2010]. As a lipid phosphatase, PTEN catalyzes conversion of phosphatidylinositol (3,4,5) triphosphate ($PIP_3$) to phosphatidylinositol (4,5) diphosphate ($PIP_2$) by dephosphorylating the 3-position of $PIP_3$, hence suppressing PI3K signaling pathway by antagonizing PI3K activity. [Di Cristofano et. al 2010]. Deletion or inactivation of PTEN enhances PI3K activity and promotes activation of downstream components of PI3K signaling pathway, including PDK1, Akt and mammalian target of rapamycin (mTOR), which leads to tumor formation [Di Cristofano et. al 2010; Stambolic et al. 1998].

Regulation of PI3K-mediated signaling by PTEN is also deeply related to nerve regeneration process in nerve system. Recent studies reveal that inhibition of PTEN protein or deletion of PTEN gene facilitates intrinsic regenerative outgrowth of adult CNS/PNS nerve upon Injury [Park et. al 2008; Liu et. al 2010; Sun et. al 2012; Christie et. al 2012]. For example, Park et al. found that deletion of PTEN in adult rat retinal ganglion cells (RGCs) using conditional knockout mice actually promotes robust axon regeneration after optic nerve injury by reactivating PI3K-Akt-mTOR signaling pathway. Reactivating mTOR pathway by conditional knockout of another negative regulator of the mTOR pathway also leads to axon regeneration, indicating that promotion of PI3K-mTOR signaling may be a key factor for restoring intrinsic axon regeneration ability. Also, Liu et al. reported that conditional deletion of PTEN in in vivo CNS injury model actually increases the diminished neuronal mTOR activity upon CNS injury by up-regulating PI3K signaling pathway, which leads to enhanced compensatory sprouting of uninjured CST axons and successful regeneration of injured CST axons past a spinal cord lesion. In case of PNS injury, inhibition of PTEN both in vitro and in vivo also increases axonal outgrowth [Christie et. al 2012]. Thus, developing PTEN inhibitor for promoting PI3K-mTOR signaling pathway is a good therapeutic target to enhance axon regeneration in injured nerve system. the PTEN inhibitor may be used in combined therapeutic methodology with existing or novel cell therapy containing other effective reagents for nerve regeneration after CNS or PNS injury.

In this study, we developed potential PTEN inhibitors effective for nerve regeneration and/or protection from nerve degeneration by stimulating PI3K signaling pathway. For activation of PTEN as lipid phosphatase, PTEN must localize in the plasma membrane in an appropriate orientation [Leslie et. al 2008]. Thus, we investigated the mechanism of PTEN membrane localization to design potential PTEN inhibitor candidates in peptide form. Three different peptides—TGN-1, TGN-2 and TGN-3—were designed and synthesized as potential PTEN inhibitors and their inhibitory ability against PTEN activity using in vitro PTEN activity assay was investigated. We also characterized their effect on regulation of PI3K signaling pathway by using neuronal cell lines. We discovered that TGN-1 and TGN-2 peptides, which are modified peptides mimicking the phosphorylation site in PTEN C-terminal region, actually diminished PTEN lipid phosphatase activity in in vitro PTEN activity assay. TGN-1 peptide also enhanced the activation level of Akt protein in PC12 cells, indicating that these peptides are effective to up-regulate PI3K-Akt signaling pathway. Neurite assay with neuronal cell showed that TGN-1 and TGN-2 peptides promoted neurite outgrowth as well as delayed neurite degeneration by enhancing neurite microtubule structure. Therefore, TGN peptides are useful as a therapeutic agent for nerve regeneration after CNS injury.

SUMMARY OF THE INVENTION

In one aspect, present invention is directed to the following:

In one aspect, the invention is directed to a method of regenerating nerve or attenuating degeneration of nerve at a site of nerve injury comprising administering at or an area near an injured nerve, a nerve regenerating or nerve degeneration attenuating amount of phosphatase and tensin homolog (PTEN) lipid phosphatase inhibiting peptide. The PTEN inhibitor peptide may be modified PTEN peptide or fragment thereof in which phosphorylation site is modified such that a serine or threonine in the phosphorylation site is phosphorylated. The phosphorylated serine or threonine may be located at position Thr-366, Ser-370, Ser-380, Thr-382, Thr-383 or Ser-385. The phosphorylated serine or threonine may be located at position Ser-370, Ser-380 and/or Ser-385. The phosphorylated serine or threonine may be located at position Ser-370, Ser-380 and Ser-385. The phosphorylated serine or threonine may be located at position Ser-380 and Ser-385. The peptide may be a fragment of a peptide of phosphorylation site and/or PDZ domain binding motif. The peptide may further comprise a peptide transfer domain (PTD). The nerve injury may be in the central nervous system.

In another aspect, the invention is directed to peptide which inhibits phosphatase and tensin homolog (PTEN) lipid phosphatase activity. The PTEN inhibitor peptide may be modified PTEN peptide or fragment thereof in which phosphorylation site is modified such that a serine or threonine in the phosphorylation site is phosphorylated. The phosphorylated serine or threonine may be located at position Thr-366, Ser-370, Ser-380, Thr-382, Thr-383 or Ser-385. The phosphorylated serine or threonine may be located at position Ser-370, Ser-380 and/or Ser-385. The phosphorylated serine or threonine may be located at position Ser-370, Ser-380 and Ser-385. The phosphorylated serine or threonine may be located at position Ser-380 and Ser-385. The peptide may be a fragment of a peptide of phosphorylation site and/or PDZ domain binding motif. The peptide may further comprise a peptide transfer domain (PTD). The nerve injury may be in the central nervous system.

In yet another aspect, the invention is directed to a method of growing, proliferating or enhancing activity of a nerve cell comprising contacting the nerve cell with tensin homolog (PTEN) lipid phosphatase inhibiting peptide.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIG. 1A) Diagram of PTEN C-terminal Region. PTEN C-terminal region include C2 domain (AA186~403), phosphorylation site (AA352~399) and PDZ domain binding motif (400~403). The phosphorylation site and PDZ domain binding motif containing region (AA352~403) were used as template for TGN peptide design. FIG. 1B) Amino acid sequence of TGN peptides. TGN-1, TGN-2 and TGN-3 peptides mimic PTEN phosphorylation site, in which the indicated residues were modified by phosphorylation. TGN-4 peptide is a scrambled peptide for TGN-1, and TGN-5 peptide is a scrambled peptide for TGN-2.

FIG. 2A) Mechanism of In vitro PTEN Activity Assay using Malachite Green Assay Kit. C8-PIP$_3$ was used as PTEN substrate and prepared as liposome with other phospholipids (DOPC and DOPC). The phosphate ions produced by PTEN from C8-PIP3 were measured by monitoring the optical density of phosphate ion-Malachite Green reagent complex at 620 nm. FIG. 2B) Effect of TGN peptides against in vitro PTEN activity. TGN-1, TGN-2 and TGN-3 peptides were examined for their PTEN inhibitory effect via in vitro PTEN activity assay. 10 µM of each peptide was incubated with 20 ng of human recombinant PTEN protein and 0.1 mM of C8-PIP$_3$ as liposome in 100 µL of reaction volume. TGN-4 and TGN-5 peptides were used to check the sequence specificity for TGN-1 and TGN-2/3 peptides, respectively. All data represent results of experimentation in triplicate. FIG. 2C) IC$_{50}$ curves for TGN-1 and TGN-2 peptides. IC$_{50}$ values were measured via in vitro PTEN activity assay with TGN-1 and TGN-2 peptides in dose-dependent manner and calculated via Prism 5 software. IC$_{50}$ values for TGN peptide are 19.93 µM for TGN-1, 4.83 µM for TGN-2 and 87.12 µM for TGN-3.

FIG. 3A) Mechanism of Akt activation by blocking PTEN activity using TGN-1. Introduction of TGN-1 in PI3K signaling pathway facilitates PI3K signaling and promotes Akt activation (phosphorylation) level. FIG. 3B) Western blot data with PC12 cell lysates. PC12 cells were treated with either TGN-1 peptide (10 µM, 100 µM) or TGN-4 peptide (10 µM) and incubated for 24 hr. Western blot data using anti-phospho Akt antibody showed that TGN-1 specifically promotes endogenous Akt activation level in dose-dependent manner. FIG. 3C) The expression level of PTEN and β-actin were also monitored as positive and loading control.

FIG. 4A) Differentiated PC12 cells were firstly treated with Nocodazole (0.5 µM) for 1 hr, and incubated with fresh media containing NGF (10 ng/mL) and TGN peptides (TGN-1 and TGN-2, 100 µM/each) for additional 72 hrs. Relative neurite stability was calculated as a ratio of green/red fluorescence signal intensities from immunofluorescence images using Image J software. All fluorescence signal intensities were measured at least 3 times per each sample for green/red ratio calculation and normalized (media only=100%). FIG. 4B) Quantification of neurite outgrowth on differentiated PC12 cells. PC12 cells were treated with differentiation medium containing NGF (50 ng/ml) for 24 hr, followed by incubation with TGN peptides (100 µM/each) for additional 2 days. TGN-4 peptide was used as a negative control for TGN-1. Neurite quantification was performed spectrophotometrically using neurite quantification kit (Millipore) at day 3 and normalized (Media only=100%).

DETAILED DESCRIPTION OF THE PREFERRED EMBODIMENTS

Figures 1A, 1B:
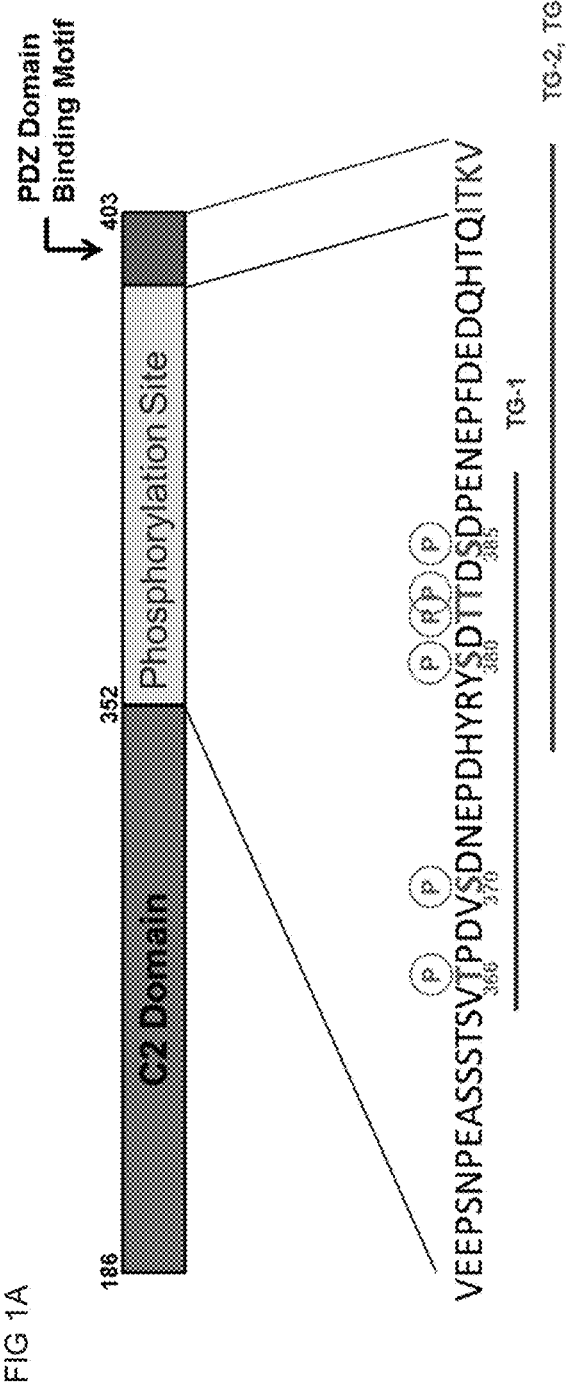
FIGS. 1A-1B show design of TGN peptides as potential PTEN inhibitor.

In the present application, "a" and "an" are used to refer to both single and a plurality of objects.

As used herein, injection of cells "near" an injured nerve or neural system is meant that area which is close enough between the injection site and the injury area to effect an efficacious outcome of regenerating nerve or preventing degeneration of the injured nerve cells at the injured site. Therefore, the injection of cells at or near an injured nerve includes at the site of injury or anywhere close enough for the injected cells to express the effective polypeptide and the polypeptides are allowed to directly or indirectly effect the nerve regeneration or nerve degeneration preventing outcome. For peripheral nerve, especially in spinal cord injury, the injection can be made "upstream" of the injury site since cells tend to leak out at the site of injury.

As used herein, "neurite" refers to any projection from the cell body of a neuron. This projection can be either an axon or a dendrite. The term is frequently used when speaking of immature or developing neurons, especially of cells in culture, because it can be difficult to tell axons from dendrites before differentiation is complete.

As used herein, "regeneration of nerve" means generation of new nerve cells, neurons, glia, axons, myelins or synapses upon nerve injury in either central nervous system (CNS) or peripheral nervous system (PNS). The regeneration is driven by restored intrinsic neuroregeneration ability via activation of PI3K-mTOR-mediated signaling by inhibition of PTEN.

As used herein, "attenuation" or "prevention" of degeneration of nerve means delaying the degeneration of axon, glia or myelin stealth structure caused by nerve injury in either central nervous system (CNS) or peripheral nervous system (PNS). The "attenuation" or "prevention" is achieved by neuronal microtubule structure stabilization closely related with PI3K-mTOR-mediated signaling, which is activated by PTEN inhibition.

Phosphatase and Tensin Homolog (PTEN)
PTEN amino acid sequence is as follows:

anchors to attach the PTEN protein on the cell membrane surface [Lee et. al 1999; Georgescu et. al 2000; Leslie et. al 2008]. Additional binding using other binding moieties is also necessary for PTEN to be properly orientated on the cellular membrane for lipid phosphatase activity of PTEN to occur [Chambell et. al 2003; Walker et. al 2004; Odriozola et. al 2007].

The unstructured part (AA 352-399) in the PTEN C-terminal region is called "phosphorylation site" because this region contains six Serine/Threonine (Thr-366, Ser-370, Ser-380, Thr-382, Thr-383, and Ser-385) residues known as phosphorylation modification sites [Lee et. al 1999; Vazquez et. al 2001]. Previous studies revealed that mutation or deletion of these 6 residues in this "phosphorylation site" leads to greater tumor suppressor activity, enhanced PTEN membrane affinity, and reduced protein stability [Vasquez et. al 2001; Das et. al 2003; Okahara et. al 2004; Randar et. al 2009].

Currently, it is believed that PTEN protein has two conformation states (FIG. 4). In the "closed" conformation, PTEN is inactive because the C-terminal region of PTEN including the "phosphorylation site" masks membrane-binding motifs located in the C2 domain as well as the PTEN active site pocket, preventing PTEN association to cell

```
                                                          (SEQ ID NO: 1)
         10         20         30         40         50         60
MTAIIKEIVS RNKRRYQEDG FDLDLTYIYP NIIAMGFPAE RLEGVYRNNI DDVVRFLDSK 70         80         90        100        110        120
HKNHYKIYNL CAERHYDTAK FNCRVAQYPF EDHNPPQLEL IKPFCEDLDQ WLSEDDNHVA 130        140        150        160        170        180
AIHCKAGKGR TGVMICAYLL HRGKFLKAQE ALDFYGEVRT RDKKGVTIPS QRRYVYYYSY 190        200        210        220        230        240
LLKNHLDYRP VALLFHKMMF ETIPMFSGGT CNPQFVVCQL KVKIYSSNSG PTRREDKFMY 250        260        270        280        290        300
FEFPQPLPVC GDIKVEFFHK QNKMLKKDKM FHFWVNTFFI PGPEETSEKV ENGSLCDQEI 310        320        330        340        350        360
DSICSIERAD NDKEYLVLTL TKNDLDKANK DKANRYFSPN FKVKLYFTKT VEEPSNPEAS 370        380        390        400
SSTSVTPDVS DNEPDHYRYS DTTDSDPENE PFDEDQHTQI TKV
```

PTEN protein is currently becoming a popular target for developing therapeutic material to regenerate injured nerve in adult CNS system by restoring diminished intrinsic nerve regeneration ability by promoting PI3K-Akt-mTOR signaling [Park et. al 2008; Liu et. al 2010; Sun et. al 2012]. Development of novel PTEN inhibitor is considered to be a good strategy for developing PTEN-activity regulating molecules. Unfortunately, the X-ray crystal structure of PTEN protein [Lee et. al 1999] is not sufficient to provide enough information for PTEN-substrate (PIP$_3$) binding status, which is critical for designing effective PTEN inhibitors directly blocking PTEN-substrate binding. Alternatively, the mechanism by which PTEN targets the plasma membrane for its activity is under intense investigation. Although the phosphatidylinositol (3,4,5) diphosphate (PIP$_3$), a substrate of PTEN enzyme, is a member of phospholipids found in the cellular membrane lipid bilayer, PTEN protein is originally produced as a soluble protein and has to be activated interfacially for its lipid phosphatase activity through conformational change, followed by PTEN-membrane association in the proper orientation [Das et. al 2003; Leslie et. al 2008]. Several charged amino acids and binding motifs located in PTEN C2 domain are considered to be the main membrane and PIP$_3$ access to the active site. On the other hand, PTEN becomes active interfacially in the "open" conformation state, where the PTEN active site pocket and C2 domain are both unmasked and totally exposed to cell membrane and its substrate PIP$_3$. Also, the phosphorylation state of these 6 Serine/Threonine residues in the "phosphorylation site" is considered to be a critical factor for PTEN interfacial activation because it directly controls conformational change of PTEN protein from "closed" conformation to "open" conformation [Das et. al 2003, Vasquez et. al 2006; Odriozola et. al 2007, Randar et. al 2009].

Figure 5:
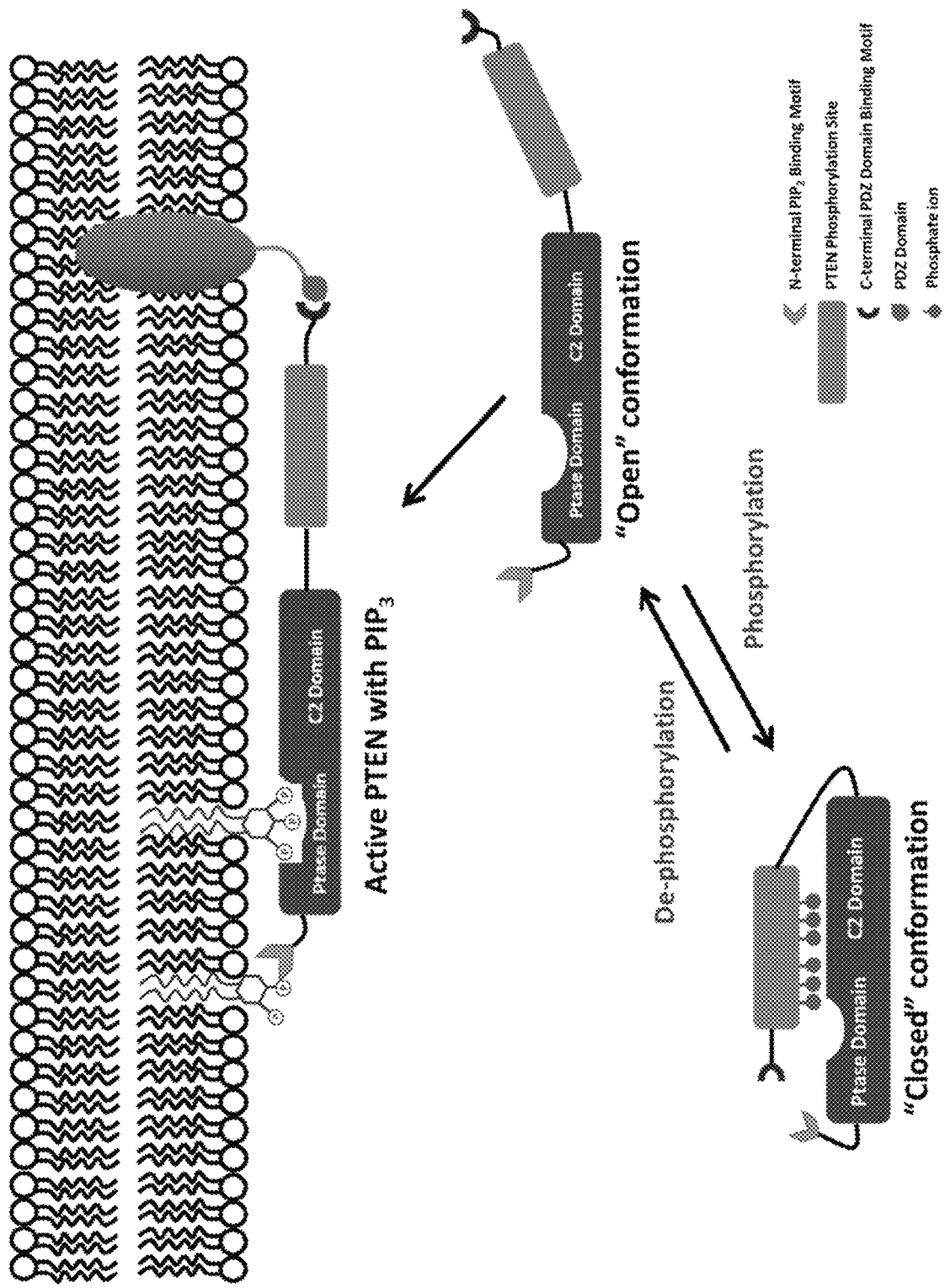
FIG. 5 shows a hypothetical model of the interfacial activation of PTEN at cell membrane surface. PTEN is currently believed to have two conformational states in vivo and is proposed to undergo conformational change to localize in the membrane localization in order to fully express its lipid phosphatase activity. Soluble form of PTEN is in inactive state with "closed" conformation, where the phosphorylated sites of PTEN C-terminal region spatially mask PTEN active site and C2 domain to prevent PTEN membrane association. When the phosphorylated residues in the "phosphorylation site" are de-phosphorylated, PTEN changes its conformation from "closed" conformation to "open" conformation. In this stage, multiple membrane-binding motifs located at C2 domain of PTEN are exposed and are ready to associate with a membrane. The binding pocket of PTEN active site is also available for accessing PIP$_3$ substrate residing on the membrane surface. Binding of PIP$_2$ on the membrane surface with N-terminal PIP$_2$ binding motif as well as the binding of C-terminal PDZ domain binding motif to PDZ domain in adjutant protein (NHERF1) follow after PTEN is localized on the cell membrane surface in its appropriate position required for its lipid phosphatase activity to occur.

According to the currently suggested model (FIG. 5), there are three steps required for the interfacial activation of PTEN at a membrane surface.

1) dephosphorylation of phosphorylated Serine/Threonine residues in the "phosphorylation site" triggers PTEN conformational change from "closed" to "open" conformation, which enables PTEN protein to associate with cellular membrane and expose PTEN active site pocket to PIP$_3$ substrate located on the cell membrane.

2) Multiple membrane-binding motifs in C2 domain then interact with cell membrane to anchor PTEN protein on the membrane surface.

3) Additional Interaction between N-terminal $PIP_2$ binding site (AA6-15) and $PIP_2$ molecule in the cellular membrane [Walker et. al 2004] as well as the binding of C-terminal PDZ domain binding site (AA400-403) with the PDZ domain of adjutant NHERF1 protein [Takahashi et. al 2006; Molina et. al 2010] are both also required for adjustment of PTEN orientation on the cellular membrane surface.

We designed our TGN peptide as potential PTEN inhibitor based on the PTEN membrane localization model shown in FIG. 4, in particular the "phosphorylation site" and PDZ domain-binding site (AA 352-403). The basic concept of TGN peptide as potential PTEN inhibitor is to prevent the association between PTEN and cell membrane surface by masking PTEN active site and the C2 domain required for membrane binding. As Ser370 and Ser385 are preferentially phosphorylated via casein kinase II [Miller et. al 2002,] membrane localization as well as phosphatase activity are increased, more than when other residues are mutated [Odriozola et. al 2007]. Therefore at least one Serine residue out of these two were included in all TGN peptides (Ser370/385 in TGN-1, Ser385 in TGN-2/TGN-3). Also, phosphorylated Serine residues at 380 and 385 positions are currently considered to be part of "pseudo-substrate", masking the catalytic pocket in PTEN active site from accessing the real substrate $PIP_3$ [Odriozola et. al 2007]. The peptides were designed to include these two Serine residues (Ser 380 and Ser 385) in all of the TGN peptides.

TGN-1 peptide sequence mimics AA 365-388 region of PTEN phosphorylation site and contains four Serine/Threonine residues (Thr366, Ser370, Ser380 and Ser385) with three phosphorylated modified residues (Ser370, Ser380 and Ser385). TGN-2 and TGN-3 peptide mimics AA376-403 region of PTEN protein, including two phosphorylated Serine residues (Ser380 and Ser385) as well as the C-terminal PDZ domain-binding motif (ITKV). Only the Serine residues in both TGN-1 and TGN-2 peptides were phosphorylated to mimic the phosphorylation site of PTEN in vivo because phosphorylation of Threonine residues results in secondary modification in vivo and is also less effective for altering PTEN-membrane binding affinity when mutated [Odriozola et. al 2007; Randar et. al 2009]. In TGN-3 peptide, two Serine residues (Ser380 and Ser385) were substituted with Valine for comparison. Additionally, the sequences of TGN-1 and TGN-2/3 peptides were scrambled to examine sequence specificity, and these peptides were designated as TGN-4 and TGN-5 peptide, respectively.

In vitro activity assay and $IC_{50}$ assay with recombinant human PTEN protein and C8-$PIP_3$ as substrate showed that TGN-1 and TGN-2 peptides specifically inhibit PTEN activity in vitro in dose-dependent manner (FIG. 2). C8-$PIP_3$ was introduced to PTEN protein as synthesized lipid vesicle—a mimicking system of cell membrane lipid bilayer—with other phospholipid molecules (DOPC/DOPS). The activity assay results implied that TGN-1 and TGN-2 peptides may inhibit in vitro PTEN activity by directly interacting with PTEN protein and interfering with PTEN-vesicle membrane association to prevent the substrate (C8-PIP3) from binding to the PTEN active site. In fact, in vitro PTEN activity assay with direct addition of C-8 PIP3 lipid only instead of the liposome form fails to show PTEN activity (data not shown). Much reduced inhibitory effect by TGN-3 peptide compared with TGN-2 peptide suggests that phosphorylation modification on the Serine residues (Ser380 and Ser385) is a significant factor for in vitro PTEN inhibition by TGN-peptide. Also, TGN-2 peptide showed nearly 4-fold higher inhibitory effect on in vitro PTEN activity than TGN-1 peptide ($IC_{50}$ value for TGN-1 is 19.93 μM and for TGN-2 is 4.83 μM). The main difference in structure between TGN-1 and TGN-2 peptides is that the TGN-2 peptide contains the last 15 amino acid sequence of PTEN C-terminal region (AA389~403) including PDZ domain binding motif (AA 399~403). Since the activity assay was performed in in vitro conditions, It may be explained that the last 15 amino acid sequence present in TGN-2 peptide either provides higher binding affinity toward PTEN protein to interfere with PTEN-vesicle membrane association more efficiently or masks the substrate binding pocket in PTEN active site more effectively than TGN-1 peptide.

TGN-1 peptide is also effective in blocking PTEN activity to regulate PI3K-Akt signaling pathway in neuronal cells (FIG. 3). PC12 cells containing endogenous or overexpressed PTEN were incubated with TGN-1 for 24 hr and the activation (phosphorylation) level of Akt protein was examined by Western blotting using anti-phospho Akt antibody. The phosphorylation level of Akt protein in cell lysates treated with TGN-1 peptide was much higher than the lysates treated with TGN-4 peptide or DMSO, indicating that TGN-1 peptide specifically inhibits PTEN to antagonize PI3K activity. Thus, TGN-1 peptide is effective in promoting PI3K-Akt signaling pathway by suppressing PTEN activity.

Since microtubule stabilization is considered to be critical for treating spinal cord injury by promoting axonal regeneration ability and neuronal polarization [Sengottuvel et al 2011, Hellal et al 2011, Witte et al 2008], we adopted Nocodazole to induce neuritic degeneration on differentiated neuronal cells and tested if TGN peptides show neuroprotective effect via microtubule stabilization. As microtubule stability is closely related to α-tubulin acetylation level [Takemura et al 1992], we immunostained stable neurites with anti-acetylated α-tubulin antibody. Immunofluorescence data (FIG. 4A) demonstrated that TGN-1 and TGN-2 peptides actually stabilized neurite microtubule structure to delay neurite degeneration. Moreover, addition of TGN-1 peptide specifically promotes neurite outgrowth on neuronal cell differentiation process (FIG. 4B). Thus, TGN-1 and TGN-2 peptides show neurotrophic effect as well as neuroprotection against neurite degeneration.

In a previous study, Odriozola et. al reported that synthetic phosphomimic peptides (Cp-23, Cp-23DE) encompassing the PTEN C-terminal phosphorylation site cluster (AA368-390), similar to TGN-1 peptide sequence, mediates the suppression of PTEN catalytic activity in vitro. Also, assays with 293T cells transfected with GFP-fused phosphomimic peptides were shown to decrease level of PTEN-membrane association and improve phospho-Akt levels. However, the phosphomimic peptides (Cp-23, Cp-23DE) used in Odriozola et al. mimics only the AA 368~390 region of PTEN "phosphorylation site" but contains no phosphorylated Serine residues as in the present TGN peptides. In fact, although the Odriozola peptide (Cp23) and TGN-1 peptide share nearly identical amino acid sequence, the inhibition potency of TGN-1 peptide is almost 50 times higher than the Odriozola peptide (Cp23) by comparing in vitro $IC_{50}$ values ($IC_{50}$ value for TGN-1 is 19.93 μM and for Cp23 is ~1033 μM). Moreover, there was nearly no difference in the $IC_{50}$ values between the Odriozola peptide (Cp23, 1033 μM) and its scrambled peptide (Cp23-Der, 945 μM). However, TGN-1 peptide showed much higher inhibitory effect than its scrambled peptide TGN-4 (FIG. 2B), indicating that the TGN-1 peptide shows sequence-specific inhibitory effect on in vitro PTEN activity when the Odriozola peptide (Cp23) failed to do. Additionally, TGN-2 peptide is different from the Odriozola peptide (Cp23) by containing additional 15 amino acid residues including the PDZ domain-binding motif, which is already shown to be effective for PTEN inhibition ($IC_{50}$ value for TGN-2 is 4.93 μM). Also, TGN-1 and TGN-2 peptides include PTD (peptide transfer domain) sequence at their N-terminal ends so that these peptides can be introduced directly into the cells, whereas the Odriozola peptides need to be fused with GFP and transfected into the cells. Thus, TGN-1 and TGN-2 peptides possess effective PTEN inhibition ability in vitro and in vivo.

We developed peptides by mimicking PTEN C-terminal region including the "phosphorylation site". TGN-1 and TGN-2 showed specific and effective inhibitory effect on PTEN activity in vitro and up-regulated PI3K-Akt signaling pathway by blocking PTEN activity in neuronal cells. Since facilitating PI3K-Akt-mTOR signaling by suppression of PTEN is known to be effective in nerve regeneration upon CNS injury [Saijilafu et al 2013], the inventive peptides are useful as therapeutic or treatment agent for CNS injury. Neurite assay using differentiated neuronal cells with TGN peptides demonstrated that TGN-1 and TGN-2 peptides clearly show neurotrophic effect, as well as neuroprotective effect on degenerated neurite by enhancing neurite microtubule structure. Thus, these peptides are therapeutic targets for nerve regeneration after nerve injury including CNS injury, as well as for delaying neurodegenerative progress.

Peptide Design

The inventive peptides, also referred to herein as "TGN peptides", as PTEN inhibitor were designed using PTEN C-terminal region (amino acid residues 352~403) as template.

It is preferred that all of the TGN peptides include PTD (peptide transfer domain) sequence, which may include RRRRRRRR (SEQ ID NO:2) at the N-terminal end to increase membrane permeability.

The TGN peptide may be any fragment of PTEN within amino acid residues 352-403 of PTEN amino acid sequence of SEQ ID NO:1, or a fragment of PTEN that includes as part of its sequence, a portion of the amino acid residues 352~403 of PTEN amino acid sequence of SEQ ID NO:1. Preferably, the TGN peptide includes phosphorylation of a Serine or Threonine present in this peptide fragment. Preferably, the Serine or Threonine sites are at 366, 370, 380, 382, 383, or 385 of the PTEN protein of SEQ ID NO:1.

The TGN peptide may be at least 10 amino acid residues long, at least 15, at least 20 at least 25, at least 30, at least 35, or at least 40 amino acid residues long. It is preferred that phosphorylation of at least one of the Serine or Threonine residue or a combination thereof is included in the peptide.

It should be recognized that in one aspect, the TGN peptide is not limited by the length of its peptide. It is preferred that at least part of the peptide resides within amino acid residues 352 to 403.

In this regard, exemplified TGN-1 peptide has 24 amino acids with three phosphorylated Serine residues VTPDVpSDNEPDHYRYpSDTTDpSDPE (SEQ ID NO:3), pS=phosphorylated Serine). When the PTD is attached at the N-terminus, RRRRRRRR-VTPDVpSDNEPDHYRYpSDTTDpSDPE-amide (SEQ ID NO:4) is seen having 32 amino acid residues.

Another exemplified peptide is TGN-2 peptide, which has 28 amino acids with two phosphorylated Serine residues HYRYpSDTTDpSDPENEPFDEDQHTQITKV (SEQ ID NO:5). When the PTD is attached at the N-terminus, RRRRRRRR-HYRYpSDTTDpSDPENEPFDEDQHTQ-ITKV-amide (SEQ ID NO:6) is seen having 36 amino acid residues.

TGN-3 peptide has the same amino acid sequence as TGN-2 peptide but no residue is modified and two Serine residues were substituted to Valine HYRYVDTTDVDPENEPFDEDQHTQITKV (SEQ ID NO:7). When the PTD is attached at the N-terminus, RRRRRRRR-HYRYVDTTDVDPENEPFDEDQHTQITKV-amide (SEQ ID NO:8) is seen.

TGN-4 peptide was designed as a scrambled peptide of TGN-1 peptide SDDEYTDNPDSRYVSDTPVDTEH (SEQ ID NO:9). When the PTD is attached at the N-terminus, RRRRRRRR-SDDEYTDNPDSRYVSDTPVDTEH-amide (SEQ ID NO:10) is seen. And TGN-5 peptide was designed for TGN-2/TGN-3 scrambled peptide DEHDTEYTPDYRQETHFNSQPTDKSDVI (SEQ ID NO:11). When the PTD is attached at the N-terminus, RRRRRRRR-DEHDTEYTPDYRQETHFNSQPTDKSDVI-amide (SEQ ID NO:12) is seen.

Chemically Modified Peptides

Polypeptide therapeutics may suffer from short circulating half-life, and proteolytic degradation and low solubility. To improve the pharmacokinetics and pharmacodynamics properties of the inventive biopharmaceuticals, methods such as manipulation of the amino acid sequence may be made to decrease or increase immunogenicity and decrease proteolytic cleavage; fusion or conjugation of the peptides to immunoglobulins and serum proteins, such as albumin may be made; incorporation into drug delivery vehicles for the biopharmaceuticals such as the inventive peptides and antibodies for protection and slow release may also be made; and conjugating to natural or synthetic polymers are also contemplated. In particular, for synthetic polymer conjugation, pegylation or acylation, such as N-acylation, S-acylation, amidation and so forth are also contemplated.

Nerve Tissue

Nervous tissue derives from the embryonic ectoderm under the influence of the notochord. The ectoderm is induced to form a thickened neural plate that then differentiates and the ends eventually fuse to form the neural tube from which all of the central nervous system derives. The central nervous system consists of the brain, cranial nerves and spinal cord. The peripheral nervous system derives from cells next to the neural groove called the neural crest.

Nerve tissue is distributed throughout the body in a complex integrated communications network. Nerve cells (neurons) communicate with other neurons in circuits ranging form very simple to very complex higher-order circuits. Neurons do the actual message transmission and integration while other nervous tissue cells called glial cells assist neurons by support, protection, defense and nutrition of the neurons. There are about 10 times more glial cells than neurons in the brain. Glial cells create the microenvironment needed for neuronal function and sometimes they assist in neural processing and activity. Neurons are excitable cells. This means that when properly stimulated, an action potential can be initiated that may be propagated over the cell membrane to transmit information to distant cells. Neurons are independent functional units responsible for the reception, transmission and processing of stimuli.

In general, neurons consist of three parts; the cell body, where the nucleus and cellular organelles are located; dendrites, which are processes extending from the cell body that receive stimuli from the environment or other neurons; and the axon, which is a long single process extending from the cell body for the transmission of nerve impulses to other cells. The axon usually branches at its distal end and each branch terminating on another cell has a bulbous end. The interaction of the end bulb with the adjacent cell forms a structure called a synapse. Synapses are specialized to receive a signal and convert it into an electrical potential.

Most neurons found in the human body are multipolar, meaning they have more than two cell processes with only one being an axon and the remaining processes being dendrites. Bipolar neurons of the retina or olfactory mucosa have one dendritic process and an axon coming off the cell body. Pseudounipolar neurons found in the spinal cord ganglia enable sensory impulses picked up by the dendrites to travel directly to the axon without passing through the cell body. Neurons may also be classified according to function. Sensory neurons are involved in the reception and transmission of sensory stimuli. Motor neurons send impulses to control muscles and glands. Other neurons, interneurons, act as go-betweens between neurons as part of functional networks.

Synapses are specialized functional cell junctions to propagate cellular signals. Most synapses are chemical synapses where vesicles in the presynaptic terminal contain a chemical messenger that is released to the synaptic cleft when the presynaptic membrane is stimulated. The chemical messenger diffuses across the synaptic cleft to bind to receptors in the postsynaptic membrane. This induces a change in the polarization state of the postsynaptic membrane effecting cellular action. A special type of synapse is the neuromuscular junction. More than 35 neurotransmitters are known and most are small molecules (nitric oxide, acetylcholine), catecholamines (norepinephrine, serotonin), or neuroactive peptides (endorphin, vasopressin). Once used, the neurotransmitters are removed quickly by enzymatic breakdown, diffusion or endocytosis by the presynaptic cell.

Some neurons are wrapped in an insulating material called myelin. This lipid rich material is formed by glial cells: Schwann cells in the peripheral nervous system and by oligodendrocytes in the central nervous system. The insulation enables faster nerve conduction by reducing the membrane surface area that must be depolarized. In myelinated neurons the nerve impulse jumps from one unmyelinated segment to another over the length of the axon. It is the myelin sheath and lack of neuron cell bodies within the tissue that makes some nervous tissue appear white as in the large peripheral nerves and white matter of the brain. Other glial cells, called astrocytes, are involved in structural integrity, neuronal nutrition and maintaining the microenvironment of nervous tissue. Astrocytes, are in direct communication with one another via gap junctions and can affect the survival of neurons in their care by the regulation of the local environment. Ependymal cells line spinal cord and the ventricles of the brain and secrete the cerebrospinal fluid. Other small glial cells, called microglia, are phagocytic cells that are involved with inflammation and repair in the adult central nervous system.

Nervous tissue is an excitable tissue that is capable of receiving and transmitting electrical impulses. The central cell type is called a neuron. Neurons usually have a cell body, dendrites that receive inputs, and an axon that transmits electrical potentials.

Neurons may be classified as sensory, motor, secretory or association neurons. They are often classified by conduction speed, diameter and the presence or absence of specialized lipoprotein insulation called myelin. Type A fibers are myelinated and can conduct impulses at 12-120 m/sec. Type B are also myelinated fibers but they only transmit impulses at 3-5 m/sec. Type C fibers are unmyelinated, small in diameter and very slow (2.5 m/sec). An example of a Type A fiber is a motor neuron innervating the gastrocnemius. An autonomic preganglionic efferent neuron is an example of a Type B fiber and a sensory neuron carrying information about diffuse pain is an example of a slow Type C fiber.

Sensory neurons are adapted to detect certain types of information from the environment. These include mechanoreceptors sensing things like pressure or stretch, thermoreceptors, photoreceptors in the retina, and chemoreceptors such as the taste bud or those for olfaction. Association neurons, or interneurons are usually found in the spinal cord and brain where they connect sensory afferent neurons to efferent motor or secretory neurons.

Neurons communicate with one another via a structure called the synapse. An axon ends in one or more terminal buttons that contain numerous small vesicles. These small vesicles are filled with chemical substances called neurotransmitters. Acetylcholine is most often the neurotransmitter at the synapse although other chemicals like norepinephrine, serotonin and GABA may be used dependent on the neuron. When an impulse travels down the axon and reaches the terminal buttons the vesicles fuse with the neuronal membrane and the neurotransmitter is released. The chemical then diffuses across the narrow synaptic cleft to specific receptors for the chemical on the postsynaptic membrane of the receiving neuron.

The interaction of the neurotransmitter with the receptor causes a change in the membrane potential that may induce a new impulse postsynaptic neuron. The enzyme acetylcholinesterase is present in synapse to break down acetylcholine and terminate the stimulus. Other neurotransmitters are either broken down or taken back up into the presynaptic neuron to terminate the stimulus.

In the central nervous system many neurons may converge on a single neuron. When each of the presynaptic neurons releases neurotransmitter into its synapse with the postsynaptic neuron, local membrane potentials occur that are integrated and summed. These incoming signals may be inhibitory or stimulatory. If the resulting summed membrane potential reaches the minimum threshold for that neuron, then an action potential will be initiated.

Action potentials travel in one direction away from the cell body by saltatory conduction. The fastest neurons are covered in myelin sheaths arranged in discreet segments separated by nodes of naked neuronal membrane called nodes of Ranvier. In saltatory conduction, the electrical potential jumps from node to node, thereby reducing the membrane area involved in conduction of the action potential and speeding up conduction.

Non-neural cells found in the nervous system are called glial cells. Astrocytes are the most numerous and provide support and nourishment of neurons. Microglia are small phagocytic cells specific to neural tissue. Cells that line the ventricular system and central canal of the spinal cord and make cerebrospinal fluid are called ependymal cells. In the central nervous system, an oligodendrocyte forms segments of the myelin sheaths of multiple neurons. In the peripheral nervous system, each segment of the myelin sheath is made by a single Schwann cell.

Central Nervous System

The central nervous system (CNS) consists of the brain and spinal cord. The meninges (dura mater, arachnoid and pia mater) protect and nourish the CNS in addition to the protection afforded by the bony skull and vertebrae. Cerebrospinal fluid is found in the subarachnoid space, central canal of the spinal column and the ventricles of the brain. The pia mater is the innermost layer and is adherant to the nervous tissue. Between the pia mater and the dura mater lies the arachnoid layer. The tough fibrous dura mater lies just beneath the skull.

The brain can be divided into 3 basic areas of the forebrain, midbrain, and brain stem. The forebrain includes the thalamus, hypothalamus, basal ganglia, and cerebrum. The cerebrum is responsible for conscious thought, interpretation of sensations, all voluntary movements, mental faculties, and the emotions.

Cerebral tissue can be divided into structural and functional areas. The surface of the cerebrum is convoluted into gyri (ridges) and sulci (grooves). The cortical sensory and motor areas can be mapped to the post central gyrus and central sulcus, respectively. The sensory area receives sensory info from the opposite side of the body that is projected after thalamic processing. Those parts of the body with more sensory nerve endings are represented by more cortical sensory area. The motor area controls voluntary muscle movements of the contralateral body parts but the association areas are important for the initiation of movement.

The cerebrum is the largest part of the brain and is divided into two hemispheres, right and left, having several lobes. The frontal lobe contains the motor area, Broca's speech area, association areas, and functions in intelligence and behavior. The parietal lobe contains sensory areas and function in feeling and hearing. Primary visual association areas are located in the occipital lobe and the temporal lobe contains areas for auditory association, smell and memory storage.

The thalamus is located between the cerebral cortex and brainstem. All sensory input except the sense of smell is processed here before being projected to other areas of the brain. The hypothalamus is located beneath the thalamus and is responsible for processing internal stimuli and the maintenance of the internal environment. Moment by moment unconscious control of blood pressure, temperature, heart rate, respiration, water metabolism, osmolality, hunger, and neuroendocrine activities are handled here. Nuclei of the neuroendocrine cells that release oxytocin and ADH from the posterior pituitary are located in the hypothalamus.

The basal ganglia (caudate nucleus, globus palladus, substantia nigra, subthalamic nucleus, red nucleus) are groups of neurons embedded within each hemisphere of the cerebrum. They are involved in the control of complex motor control, information processing and unconscious gross intentional movements.

The brainstem includes the medulla oblongata and pons. The medulla oblongata contains important functional areas and relay centers for the control of respiration, cardiac and vasomotor reflexes. The pons contains the pneumotaxic center which is involved in the regulation of respiration.

The cerebellum lies above the brainstem and uses sensory information processed elsewhere about the position of the body, movement, posture and equilibrium. Movements are not initiated in the cerebellum but it is necessary for coordinated movement.

Peripheral Nervous System

The peripheral nervous system includes nerves, ganglia, spinal and cranial nerves located outside the brain and spinal cord. The twelve cranial nerves arise from nuclei located in the brainstem and travel to specific locations carrying impulses to control various autonomic functions like smell, vision, salivation, heart rate and cutaneous sensation. Cranial nerves are often mixed in that they carry sensory and motor components but they may have only motor or sensory fibers. The following table lists the cranial nerves and their functions.

TABLE 1

Cranial Nerves

| Number | Name | Function |
| --- | --- | --- |
| I | Olfactory | Sense of smell |
| II | Optic | Vision |
| III | Oculomotor | Motor control of some eye muscles and eyelid |
| IV | Trochlear | Motor control of some eye muscles |
| V | Trigeminal | Chewing muscles and some facial sensation |
| VI | Abducent | Motor control of some eye muscles |
| VII | Facial | Motor control of facial muscles, salivation. Taste and cutaneous sensations. |
| VIII | Acoustic | Equilibration, static sense and hearing |
| IX | Glossopharyngeal | Salivation, sensations of skin, taste and viscera |
| X | Vagus | Motor control of the heart and viscera, sensation from the thorax, pharynx and abdominal viscera |
| XI | Accessory | Motor impulses to the pharynx and shoulder |
| XII | Hypoglossal | Motor control of the tongue, some skeletal muscles, some viscera, sensation from skin and viscera |

The sensory division of the peripheral nervous system takes input from various types of receptors, processes it and sends to the central nervous system. Sensory input can come from internal sources as in proprioception (sense of position of the joints and muscles) or external sources as in the sensation of pressure or heat on the skin. Areas of the skin innervated by specific spinal nerves are called dermatomes. Afferent fibers collect sensory input and travel up the spinal cord, converge in the thalamus, and end finally on the sensory cortex of the cerebrum. Those areas with more sensory receptors, i.e. the fingertips or lips, correspond to a larger area on the sensory cortex of the brain. Fibers carrying proprioceptive information are dispersed to the cerebellum as well. Almost all sensory systems transmit impulses to parts of the thalamus. The cerebral cortex is involved in conscious perception and interpretation of sensory stimuli.

Motor inputs to muscles and glands occur via the autonomic and somatic efferent systems. CNS innervation of the joints, tendons and muscles travel via the somatic efferent system. Some muscular responses are handled via spinal reflexes. An example of this is the withdrawal reflex seen when the finger contacts a hot stove. The movement to remove the finger occurs via a simple spinal reflex long before the sensation of pain reaches the brain. Clearly this is protective mechanism to avoid further injury. Motor inputs to glands and smooth muscle usually occur via the autonomic system.

Most organs receive input from both branches of the autonomic nervous system. One branch will generally be excitatory while the other is inhibitory in that organ or tissue. The sympathetic branch of the autonomic system acts to prepare the body for physiologic stress. Stimulation of the sympathetic branch is like stepping on the gas in that the body prepares to run or fight in response. Effects such as an increased heart rate, dilation of airways and mobilization of glucose from glycogen stores are seen. Sympathetic nerves arise from the $1^{st}$ thoracic to the $4^{th}$ lumbar vertebra. They have a short preganglionic neuron that ends in one of the chain ganglia that lie along the spinal column. Acetylcholine is the neurotransmitter at the synapse with the long post-ganglionic neuron which then travels to the target tissue where norepinephrine is released at the majority of sympathetic nerve endings. A few sympathetic post ganglionic neurons, such as those innervating sweat glands or skeletal muscle vasculature, release acetylcholine.

The parasympathetic branch acts to counterbalance the sympathetic branch via neurons that arise from the cranial and sacral regions of the CNS. For instance, parasympathetic stimulation constricts airways and decreases heart rate. It regulates resting activities such as digestion, micturation and erection. Long preganglionic neurons release acetylcholine at synapses close to the end organ. Short postganglionic neurons also release acetylcholine on the effector tissue.

Therapeutic Composition

In one embodiment, the present invention relates to treatment for various diseases that are characterized by neurodegeneracy. In this way, the inventive therapeutic compound may be administered to human patients who are either suffering from, or prone to suffer from the disease by providing compounds that inhibit neuronal degeneration. In particular, the disease is associated with neurodegenerative disorder of the brain, loss of nerve cell, particularly in the hippocampus and cerebral cortex, reduced neurotransmitters, cerebrovascular degeneration, crushed nerve in the spine, and/or loss of cognitive ability.

The formulation of therapeutic compounds is generally known in the art and reference can conveniently be made to Remington's Pharmaceutical Sciences, 17th ed., Mack Publishing Co., Easton, Pa., USA. For example, from about 0.05 μg to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (eg using slow release molecules by the intraperitoneal route or by using cells e.g. monocytes or dendrite cells sensitised in vitro and adoptively transferred to the recipient). Depending on the route of administration, the peptide may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 μg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and manner of administration of the said ingredients.

Delivery Systems

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, i.e., the brain, thus requiring only a fraction of the systemic dose.

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1—Materials and Experimental Methods

Example 1.1

Rat adrenal medullary PC12 pheochromocytoma neuronal cell was purchased from ATCC (Manassas, Va.). Cell culture materials including Dulbecco's modified Eagle's medium (DMEM), fetal bovine serum (FBS) and horse serum were purchased from Mediatech Inc. (Manassas, Va.). 2.5 S Nerve growth factor was purchased from BD Biosciences, Inc. (Bedford, Mass. 01730). TUJ-1 monoclonal rabbit antibody against neuronal class III β-tubulin was purchased from Covance Inc. (Gaithersburg, Md.). Monoclonal mouse antibody against acetylated α-Tubulin was purchased from Santa Cruz Biotech Inc. (Santa Cruz, Calif.). Goat serum, Texas Red® Goat Anti-Rabbit IgG antibody, Alexa Fluor® 488 Goat anti-Mouse IgG antibody, 4',6-Diamidino-2-Phenylindole, Dilactate (DAPI) and AlamarBlue® were purchased from Molecular Probes-Invitrogen (Eugene, Oreg.). Nocodazole was purchased from Sigma-Aldrich (St. Louis, Mo.). Neurite Outgrowth Assay Kit was purchased from Millipore (Billerica, Mass.). All lipids were purchased from Avanti Polar Lipids, Inc. (Alabaster, Ala. 35007). Recombinant human PTEN protein and Malachite Green phosphate detection kit were purchased from R&D Systems, Inc. (Minneapolis, Minn. 55413). Human PTEN c-DNA was purchased from OriGene Inc. (Rockville, Md. 20850). Lipofectamine™ 2000 Transfection Reagent was purchased from Invitrogen™. Tris-Glycine gradient mini gel (10~20%) was purchased from Novex™. All antibodies were purchased from Santa Cruz Biotechology, Inc. (Santa Cruz, Calif. 95060). All other materials were purchased from Fisher Scientific Inc.

Example 1.2—Peptide Design

TGN peptides as potential PTEN inhibitor were designed using PTEN C-terminal region (AA352~403) as template. All TGN peptides include PTD (peptide transfer domain) sequence (RRRRRRRR) at their N-terminal end to increase membrane permeability. TGN-1 peptide has 32 amino acids with three phosphorylated Serine residues (MW=4244.18 Da, sequence: RRRRRRRR-VTPDVpSDNEPDHYRYpS-DTTDpSDPE-amide (SEQ ID NO:4), pS=phosphorylated Serine). TGN-2 peptide has 36 amino acids with two phosphorylated Serine residues (MW=4776.28 Da, sequence: HYRYpSDTTDpSDPENEPFDEDQHTQITKV-amide (SEQ ID NO:6), pS=phosphorylated Serine). TGN-3 peptide has the same amino acid sequence as TGN-2 peptide but no residue is modified and two Serine residues were substituted to Valine (MW=4640.99 Da, sequence: RRRRRRRR-HYRYVDTTDVDPENEPFDEDQHTQ-ITKV-amide (SEQ ID NO:8)). TGN-4 peptide was designed as a scrambled peptide of TGN-1 peptide (MW=4004.19 Da, sequence=RRRRRRRR-SDDEYTDNPDSRYVSDT-PVDTEH-amide (SEQ ID NO:10)) and TGN-5 peptides was designed for TGN-2/TGN-3 scrambled peptide (MW=4616.88 Da, sequence=RRRRRRRR-DEHDTEYTP-DYRQETHFNSQPTDKSDVI-amide (SEQ ID NO:12)). All peptides were synthesized by 21$^{st}$ Century Biochemicals Inc. (Marlboro, Mass. 01752). Purity was >95% and confirmed by HPLC.

Example 1.3—In Vitro PTEN Activity Assay

In vitro PTEN activity assay was designed to check PTEN lipid phosphatase activity to convert phosphatidylinositol triphosphate ($PIP_3$) to phosphatidylinositol diphosphate ($PIP_2$) and produce phosphate ion ($P_i$). 1,2-dioctanoyl-sn-glycero-3-phospho-(1'-myo-inositol-3,4,5-triphosphate) (C8-$PIP_3$) was used as PTEN substrate and prepared as lipid vesicle (liposome) with other phospholipids because PTEN as lipid phosphatase is an interfacial enzyme. For liposome preparation, C8-$PIP_3$, DOPS (1,2-dioeloyl-sn-glycero-phosphoserine) and DOPC (1,2-dioeloyl-sn-glycero-phosphocholine) were mixed together with 800 μL of liposome buffer (50 mM Tris, 100 mM NaCl, 10 mM $MgCl_2$, 5 mM DTT, pH=8.0) to final concentration of 0.1 mM of C8-$PIP_3$, 0.25 mM DOPS and 0.25 mM DOPC. The lipid mixture was then sonicated at 4° C. for 30 min to produce liposome. After sonication, the liposome solution was briefly centrifuged to remove remaining lipids.

For PTEN activity assay, 20 ng of recombinant human PTEN protein was mixed with 40 μL of completed liposome solution. PTEN assay buffer (1 mM Tris, 20 mM DTT and 0.5% NP-40, pH=8.0) was added up to 100 μL as final volume. The reaction mixture then was incubated at 37° C. water bath for 30 min. After incubation, the inorganic phosphate ions produced by PTEN protein was detected using Malachite Green phosphate detection kit. Firstly, 50 or 100 μL of each reaction mixture was transferred to 96-well plate and 10 or 20 μL of Malachite reagent A, respectively, was added and incubated at room temperature for 10 min. After the incubation was finished, 10 or 20 μL of Malachite reagent B was added again to each sample and further incubated for 20 minutes at room temperature. Detection of the phosphate ions was performed by measuring OD (optical density) at 620 nm using spectrophotometer. For determining the inhibitory effect of TGN peptides (10 μM) on recombinant PTEN activity, each TGN peptide was prepared in DMSO solution at 1 mM concentration, and 1 μL of the TGN peptide solution was mixed with recombinant PTEN protein, liposome and PTEN assay buffer and assayed for PTEN activity by following the above protocol.

Example 1.4—In Vitro $IC_{50}$ Assay $IC_{50}$ values were measured by performing in vitro PTEN activity assay with different concentrations of TGN-1 and TGN-2 peptides. The concentration range of TGN-1 or TGN-2 peptides for $IC_{50}$ assay were 0.1, 1, 10, 30, 60, and 100 μM and 0.05, 0.1, 0.5, 1, 5, 10, and 100 μM, respectively. All data represent experimentation in triplicate and the $IC_{50}$ values were calculated by Prism 5 software (GraphPad Software).

Example 1.5—PC12 Cell Culturing

PC12 rat pheochromocytoma cells were seeded to 6-well plate ($0.6 \times 10^6$ cells/well) and cultured with DMEM media containing 7.5% FBS and 7.5% Goat Serum. After the cell confluency reached around 60~70%, NGF (nerve growth factor, 50 ng/mL) was added to the PC12 cells for differentiation and incubated for 5 more days. Then, fresh media containing different amounts of TGN peptides in DMSO solution were added to each well and incubated further for 24 hr. For PTEN overexpession, PC12 cells were seeded in 6-well plate ($1.0 \times 10^6$ cells/well) and differentiated with NGF (50 ng/mL) as above. DNA-Lipofectamine 2000 mixture was prepared for each well of cells to be transfected by firstly adding 2~2.5 μg of human PTEN c-DNA into 500 μl of Opti-MEM. 3.75-8.75 μl of Lipofectamine 2000™ reagent was added next to the above diluted DNA solution, mixed gently and incubated for 25 minutes at room temperature. Growth media of PC12 cells in 6-well plate was exchanged with fresh media and 500 μl of the DNA-Lipofectamine 2000 complex was added to each well for transfection. Transfected cells were incubated at 37° C. in 5.0% $CO_2$ incubator for 24-48 hours post-transfection before assaying for transgene expression.

Example 1.6—Neurite Assay with PC12 Cells

Rat adrenal medullary PC12 rat pheochromocytoma neuronal cells were supplemented with 7.5% fetal bovine serum (FBS), 7.5% horse serum (ES) and 0.5% penicillin streptomycin in T-75 $cm^2$ flasks that were maintained at 37° C. in a 5% $CO_2$ incubator. Cells were split at 50% confluence by gently mechanically detaching them from the flask and propagated at a split ratio 1:7.

For neurite protection assay, PC12 cells were seeded to 6-well plates with seeding density of $2.08 \times 10^5$ cells/scaffold (empirically determined as optimal seeding density) and incubated for 24-48 hr until cell confluency was reached to 60~70%. PC12 cells were then differentiated with NGF (50 ng/mL) for 72-120 hr. To mimic neurite degeneration, the differentiated PC12 cells were treated with Nocodazole (0.5 μM). After 1 hr incubation at 37° C., the old media containing Nocodazole were switched with fresh media containing NGF (10 ng/mL) and/or TGN peptides (100 μM as final concentration) and for additional 72 hrs. Remaining neurites were analyzed via immunofluorescence assay described below.

For neurite outgrowth assay, PC12 cells were seeded to 6-well plate with $1.0 \times 10^5$ cells/well seeding density. After cell confluence reached 60~70%, differentiation of the PC12 cells was initiated by adding NGF (50 ng/mL). After 24 hr of incubation, TGN peptides (50 µM as final concentration) were added to the wells in 6-well plates and incubated for two additional days. Neurite status was quantified with spectrophotometer using Neurite Outgrowth Kit (Millipore) described below.

Example 1.7—Western Blotting

After culturing, PC12 cells were collected from the 6-well plate and centrifuged down with bench-top centrifuger to make cell pellet (13,000 rpm, 5 min at RT). Supernatant was discarded and the cell pellet was resuspended with 3~500 µL of 1×PIPA buffer (Invitrogen). Resuspended cells were lysed by freezing-thaw cycle using liquid nitrogen and 37° C. water bath (3-4 times), followed by repeated spraying of resuspended cells using syringe with 27G needle. The lysed cells were centrifuged at 10,000 g for 20 min at 4° C. and the supernatants were collected and assayed for total protein concentration using BCA protein concentration kit (Thermo Scientific.).

Western blotting was performed to examine the phosphorylation level of endogenous Akt protein in PC12 cells using anti-phospho Akt antibody. SDS-PAGE was performed using Novex™ gradient mini gel (10~20%). The cell lysate samples and proteins in SDS-PAGE gel were transferred on to PVDF membrane, followed by incubation with blocking solution (5% milk in 1×TBS buffer containing 0.1% Tween-20). Anti-phospho Akt antibody was used as primary antibody with 1:500 dilution (1×TBS buffer containing 0.1% Tween-20). HRP-conjugated anti-rabbit antibody was used as secondary antibody with 1:8000 dilution factor. The expression level of endogenous or overexpressed PTEN protein was also examined using anti-PTEN antibody (1:400 dilution factor). β-actin expression level was also assayed for loading control.

Example 1.8—Neurite Quantification

For quantification of total neurites, we used Neurite Outgrowth Assay Kit (Millipore) with spectrophotometer. After the underside of the Millicell inserts (EMD Millipore, Billerica, Mass., USA) was coated with fresh extracellular matrix (ECM) protein (10 µg/mL collagen) for 2 hours at 37° C., PC12 cells were seeded per insert, that were placed into each well of a 24 well plate. Cells were kept at room temperature for 15 minutes for attachment, and then a total of 700 µl differentiation medium was added per well (600 µl and 100 µl, below and above the membrane, respectively). Neurites were left to extend for 3 days and then the inserts were fixed with −200° C. methanol for 20 minutes at room temperature, followed by fresh PBS rinse. Next, inserts were placed into 400 µl neurite staining solution for 30 minutes at room temperature, and after cell bodies were removed by a moistened cotton swab, each insert was placed onto 100 µl Neurite Stain Extraction Buffer (Millipore). Finally, the solutions were transferred into a 96 well plate and quantified on a spectrophotometer by reading absorbance at 562 nm.

Example 1.9—Immunofluorescence

After cell culture, growth media were removed and the cells were fixed with 10% formalin at room temperature for 15 minutes. Afterward, the cells were washed with a 0.5M glycine solution in PBS and blocked overnight at 40° C. with 5% Goat Serum and 0.2% Triton-X solution in PBS. For immunostaining with primary antibodies, cells were incubated overnight at 40° C. with TUJ-1 monoclonal rabbit antibody against neuronal class III β-tubulin (1:200 dilution) for total neurite staining and with monoclonal mouse antibody against acetylated α Tubulin (1:100 dilution) for stable neurite staining. Once cells were washed three times with 1×PBS buffer (10 minutes/wash), secondary antibodies— Texas Red® goat anti rabbit IgG (1:200 dilution) for TUJ-1 antibody and Alexa Fluor® 488 goat anti mouse IgG (1:200 dilution) for acetylated α Tubulin antibody—were added and incubated overnight at 40° C. Subsequently, the cells were washed three times in 1×PBS buffer (10 minutes/wash) and 1 µg/ml 4', 6-Diamidino-2-Phenylindole; Dilactate (DAPI) was added after the second washing step for staining cell nuclei. After final washing, cells were prepared to be examined using fluorescence microscope. The excitation and emission wavelengths are 488 nm/519 nm for Alexa Fluor® 488-IgG (green), and 595/615 nm for Texas Red® goat anti rabbit IgG (red) and 405/461 nm for DAPI. Fluorescence images of the cells were acquired at different magnifications and analyzed by "ImageJ" image processing and analysis program (Public Domain by Wayne Rasband, NIH, Bethesda, Md., USA).

Example 2—Results

Example 2.1—TGN Peptides were Designed Using PTEN Phosphorylation Site as Template Blocking of PTEN activity as lipid phosphatase in vivo is known to be effective in axon regeneration after nerve injury [Park et. al 2008, Christie et. al 2012]. We investigated PTEN-membrane association mechanism for designing potential PTEN inhibitor that blocks PTEN localization on cell membrane surface. According to previous studies [Lee et. al 1999; Leslie et. al 2008], PTEN protein has two functional domains—phosphatase domain and C2 domain— and also possesses "phosphorylation site" in the C-terminal region, which acts as a "switch" to control conformational change of PTEN protein via phosphorylation-dephosphorylation process [Das et. al 2003; Leslie et. al 2008]. For full lipid phosphatase activity of PTEN, dephosphorylation of phosphorylated serine/tyrosine residues at the "phosphorylation site" should occur in order to change PTEN conformation before PTEN-membrane association. Additional binding via N-terminal PIP2 binding motif and C-terminal PDZ domain binding motif localizes PTEN protein on cell membrane in appropriate position required for full PTEN activity [Walker et. al 2004; Molina et. al 2010]. Thus, we decided to use PTEN "phosphorylation site" plus PDZ-domain binding motif as a template for designing TGN peptides as potential PTEN inhibitor by disrupting PTEN-membrane association (FIG. 1A).

TGN-1 peptide mimics the amino acid sequence (365-388) of the "phosphorylation site" and TGN-2 and TGN-3 peptides mimic the amino acid sequence (376-403) of C-terminal region including the "phosphorylation site" and PDZ domain binding motif (399-403). Since phosphorylation at serine residues in the "phosphorylation site" is critical for PTEN conformation change [Leslie et. al 2008; Odriozola et. al 2007], TGN-1 peptide is modified to include three Serine residues phosphorylated (Ser 370, Ser380 and Ser385) inside the "phosphorylation site". TGN-2 peptide includes two phosphorylated serine residues (Ser380 and Ser385). In TGN-3 peptide, two serine residues (Ser380 and Ser385) were exchanged to Valine for comparison. TGN-4 and TGN-5 peptide were designed to scramble TGN-1 and TGN-2 peptide sequences, respectively. All TGN peptides were also modified to be include eight Arginine residues as peptide transfer domain (PTD) at the N-terminus to increase cell membrane permeability (FIG. 1B).

Figure 2A:
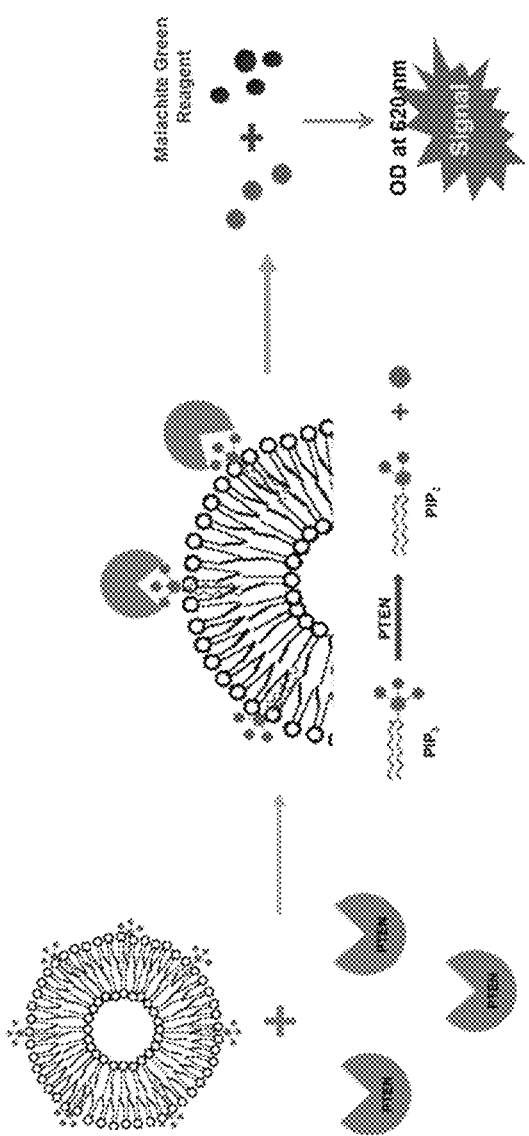
FIGS. 2A-2C show In vitro PTEN Activity Assay with TGN Peptides.
Figure 2C:
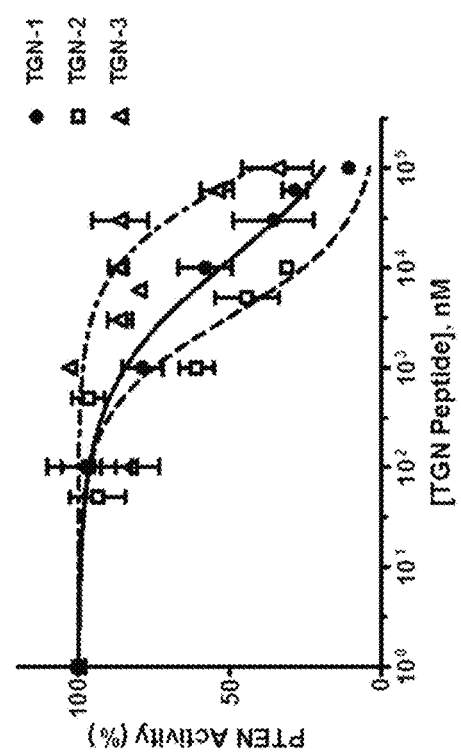
Figure 2B:
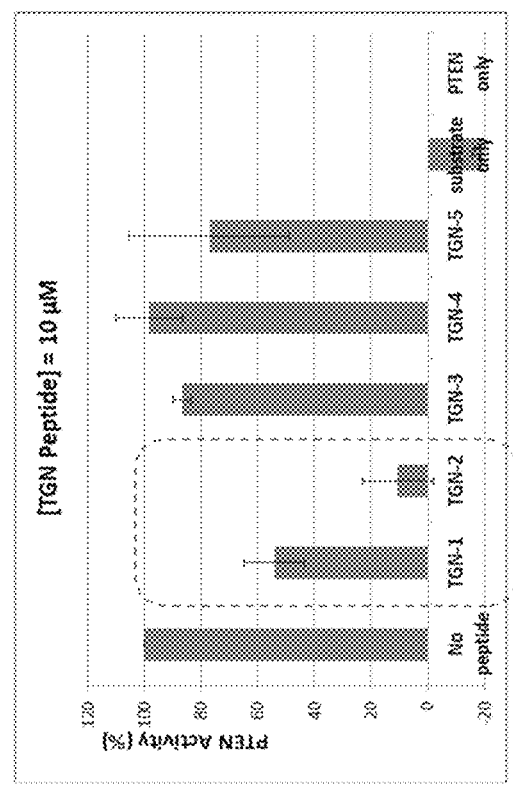

Example 2.2—TGN-1 and TGN-2 Peptides Shows Specific Inhibitory Effect on In Vitro PTEN Activity Synthesized TGN peptides were tested for their PTEN inhibitory effect using in vitro PTEN activity assay. Dioctanoyl phosphatidylinositol 3,4,5 triphosphate (diC8-$PIP_3$) was chosen as a substrate for PTEN and prepared as lipid vesicle (liposome) with two different phospholipids—dioleoyl phosphatidylcholine (DOPC) and dioleoyl phosphatidylserine (DOPS). Lipids were mixed with liposome buffer and became liposome by sonication (total lipid concentration=0.6 mM). Prepared liposome (0.1 mM of di-C8 $PIP_3$) was incubated with 20 ng of recombinant human PTEN protein for 30 minutes at room temperature to assay for PTEN activity by converting C8-PIP3 to C8-PIP2 and producing phosphate ions. The phosphate ions produced by PTEN were measured using Malachite Green reagent kit (FIG. 2A). 10 µM of each TGN peptide was examined for its inhibitory effect on PTEN activity. As seen in FIG. 2B, both TGN-1 and TGN-2 peptides significantly blocked PTEN activity (PTEN activity was decreased to 54% with TGN-1 and 31% with TGN-2 compared with positive control). On the other hand, TGN-2 peptide showed limited inhibition compared with TGN-1 or TGN-2 (86%). Also, TGN-4 and TGN-5 peptides both showed no significant inhibition of PTEN activity, indicating that PTEN inhibition by TGN-1 and TGN-2 peptides is sequence-specific. In vitro PTEN activity assay using recombinant PTEN protein and diC8-$PIP_3$ lipid molecule only failed to show PTEN activity (data not shown).

$IC_{50}$ values for TGN peptides were also measured using in vitro PTEN activity with TGN peptides in dose-dependent manner (0~100 µM range). The calculated $IC_{50}$ values for TGN-1, TGN-2 and TGN-3 peptides were 19.93 µM, 87.12 µM and 4.83 µM, respectively (FIG. 2C).

Example 2.3—TGN-1 Peptide Promotes PI3K-Akt Signaling Pathway In Vivo

Figure 3B:
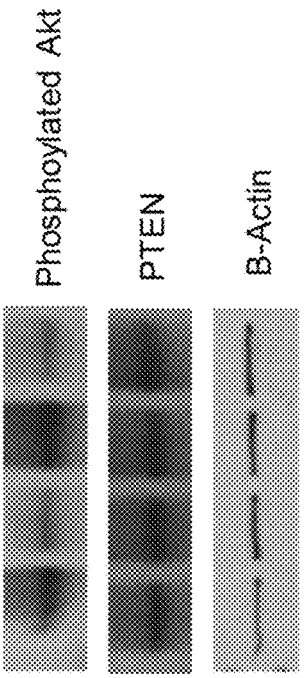
FIGS. 3A-3C show that TGN-1 peptide promotes PI3K-Akt signaling by increasing Akt activation level in vivo.
Figure 3C:
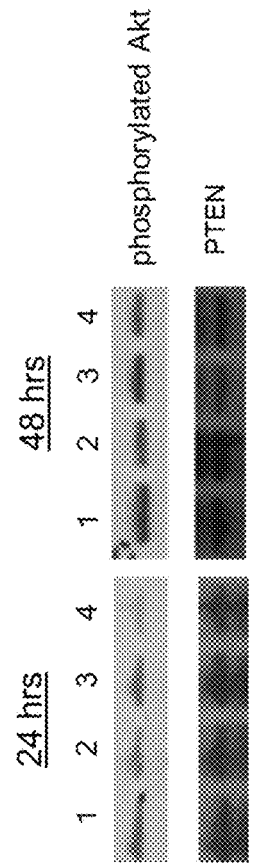
Figure 3A:
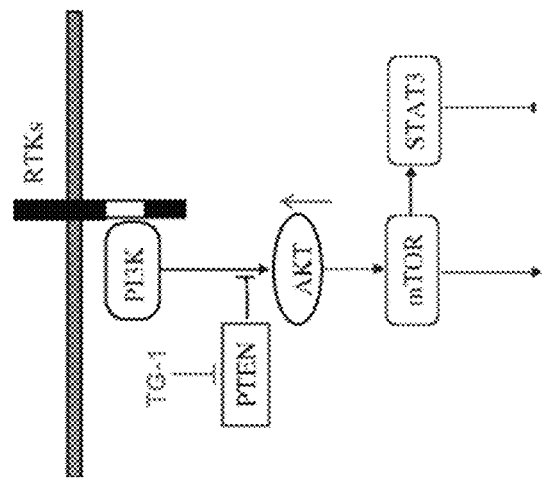

The effect of TGN-1 peptide on PI3K signaling pathway in neuronal cells was determined with PC12 rat pheochromocytoma cell line. Differentiated PC12 cells, either transfected with PTEN c-DNA for PTEN overexpression or in the natural state, were incubated with TGN-1 peptide (10 µM and 100 µM) or TGN-4 peptide (10 µM) at 37° C. for 24 hr. As seen in the diagram in FIG. 3A, if the TGN-1 peptide actually blocks PTEN activity and suppresses antagonizing effect of PTEN on PI3K activity, the activation (phosphorylation) level of Akt protein in PI3K signaling pathway should be increased. Western blot data using anti-phospho Akt protein antibody showed that the activation (phosphorylation) level of endogenous Akt protein in PC12 cells treated with TGN-1 peptide increased in TGN-1 peptide dose-dependent manner (FIGS. 3B and 3C). PC12 cells treated with either TGN-4 peptide or DMSO did not increase the activation level of AKT protein, suggesting that promotion of Akt protein phosphorylation level was specifically triggered by TGN-1 peptide. As the expression level of either endogenous PTEN (FIG. 3B) or overexpressed PTEN (FIG. 3C) showed no difference in activity upon treatment with TGN peptides or DMSO, it is clear that TGN-1 peptide specifically inhibits PTEN activity to suppress down-regulation effect of PTEN on PI3K signaling pathway and facilitate PI3K-Akt signaling pathway.

Figure 4A:
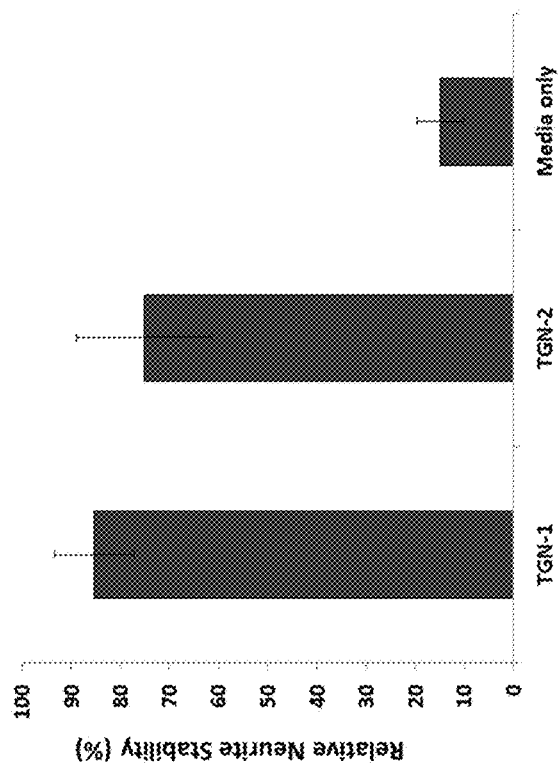
FIGS. 4A-4B show TGN-1 and TGN-2 peptide that show neurotrophic effects and neuroprotection effect against neurite degeneration.
Figure 4B:
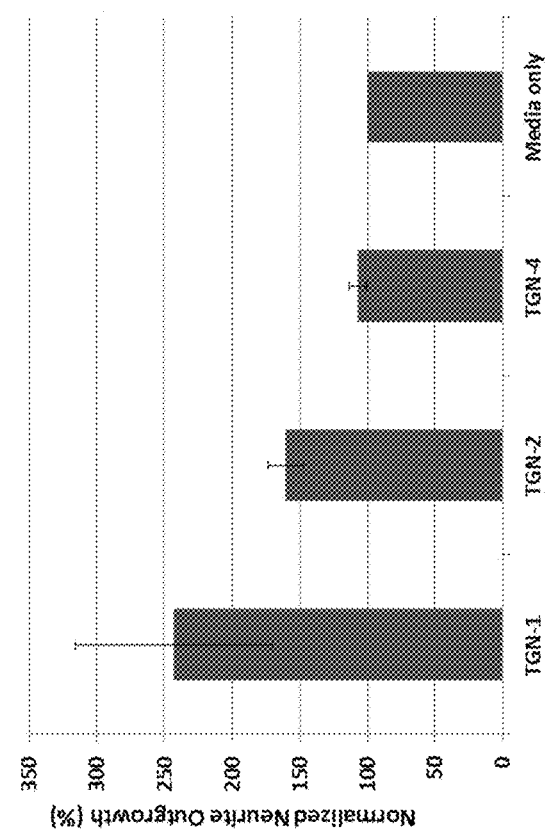

Example 2.4—TGN-1 and TGN-2 Peptides Show Neurotrophic Effects Including Neuroprotection in Neuronal Cell Culture We investigated the effect of TGN peptides against neurite degeneration on differentiated neuronal cells. Neurite degeneration was induced in PC12 cells by interfering with the cells' neuritic microtubule dynamics by contacting the cells with Nocodazole. Differentiated rat PC12 cells were treated with Nocodazole (0.5 µM) first and incubated with fresh media containing NGF (50 ng/mL) and TGN peptides (100 µM) for 72 hrs. Immunofluorescence analysis using two different tubulin antibodies (acetylated α-tubulin antibody for stable neurites and TUJ-1 β-tubulin antibody for total neurites) demonstrated that TGN-1 and TGN-2 peptides clearly delayed Nocodazole-induced neurite degeneration via microtubule stabilization (FIG. 4A). We further investigated the effect of TGN peptides on neurite outgrowth of PC12 cells. Addition of TGN peptides to the differentiating PC12 cells actually promoted neurite development (2.4-time increment by TGN-1 and 1.6-time increment by TGN-2, FIG. 4B). Taken together, we TGN-1 and TGN-2 peptides show neurotrophic effect as well as the activity of protecting mature neurites from degeneration.

REFERENCES

Campbell, R. B., Liu, F., and Ross, A. H. "Allosteric Activation of PTEN Phosphatase by Phosphatidylinositol 4,5-Bisphosphate", *J. Biol. Chem.,* 2003, 278, pp. 33617-33620.

Christie, K. J., Webber, C. A., Martinez J. A., Singh, B. and Zochodne, D. W. "PTEN Inhibition to Facilitate Intrinsic Regenerative Outgrowth of Adult Peripheral Axons.", *J. Neuro. Sci.,* 2010, 30(27), pp. 9306-9315.

Das, S., Dixon, J. E. and Cho, W. "Membrane-binding and activation mechanism of PTEN", *PNAS,* 2003, 100(13), pp. 7491-7496.

Di Cristofano, A. and Pandolfi, P. P. "The multiple roles of PTEN in tumor suppression", *Cell,* 2000, 100, (4), pp. 387-390.

Filbin, M. T. "Recapitulate development to promote axonal regeneration: good or bad approach?", *Philos. Trans. R. Soc. London B Biol. Sci.,* 2006, 361, pp. 1565-1574.

Fitch, M. T., Silver, J. "CNS injury, glial scars, and inflammation: Inhibitory extracellular matrices and regeneration failure.", *Exp Neurol.,* 2008, 209, pp. 294-301.

Georgescu, M. M., Kirsch, K. H., Kaloudis, P., Yang, H., Pavletich, N. P. and Hanafusa, H. "Stabilization and productive positioning roles of the C2 domain of PTEN tumor suppressor.", *Cancer Res.,* 2000, 60, pp. 7033-7038.

Goldberg, J. L., Klassen, M. P., Hua, Y. and Barres, B. A. "Amacrine-Signaled Loss of Intrinsic Axon Growth Ability by Retinal Ganglion Cells.", *Science,* 2002, 296, pp. 1860-1864.

Hellal, F. et al. Microtubule stabilization reduces scarring and causes axon regeneration after spinal cord injury", *Science,* 2011; "331, pp. 928-931.

Lee, J. O., Yang, H., Georgescu, M. M., Di Cristofano, A., Maehama, T., Shi, Y., Dixon, J. E., Pandolfi, P., and Pavletich, N. P. "Crystal Structure of the PTEN Tumor Suppressor: Implications for Its Phosphoinositide Phosphatase Activity and Membrane Association", Cell, 1999, 99, pp. 323-334.

Leslie, N. R., Batty, I. H., Maccario, H., Davidson, L. and Downes, C. P. "Understanding PTEN regulation: $PIP_2$, polarity and protein stability", Oncogene, 2008, 27, pp. 5464-5476.

Liu, K. et. al. "PTEN deletion enhances the regenerative ability of adult corticospinal neurons.", Nat. Neurosci., 2010, 13, pp. 1075-1081.

Miller, S. J., Lou, D. Y., Seldin, D. C., Lane, W. S., and Neel, B. G. "Direct identification of PTEN phosphorylation sites.", FEBS Lett., 2002, 528, pp. 145-153.

Molina, J. R., Morales, F. C., Hayashi, Y., Aldape, K. D. and Georgescu, M-M. "Loss of PTEN Binding Adapter Protein NHERF1 from Plasma Membrane in Glioblastoma Contributes to PTEN Inactivation", Cancer Res., 2010, 70(17), pp. 6697-703.

Odriozola, L., Singh, G., Hoang, T. and Chan, A. M. "Regulation of PTEN Activity by Its Carboxyl-terminal Autoinhibitory Domain", Jol. Bio. Sci., 2007, 282(32), pp. 23306-23315.

Okahara, F., Ikawa, H., Kanaho, Y., and Maehama, T. "Regulation of PTEN Phosphorylation and Stability by a Tumor Suppressor Candidate Protein", J. Biol. Chem., 2004, 279, pp. 45300-45303.

Park, K. K., et al. "Promoting axon regeneration in the adult CNS by modulation of the PTEN/mTOR pathway.", Science, 2008, 322, pp. 963-966.

Randar, M., Inoue, T., Meyer, T., Zhang, J., Vazquez, F. and Devreotesa, P. N. "A phosphorylation dependent intramolecular interaction regulates the membrane association and activity of the tumor suppressor PTEN", PNAS, 2009, 106(2), pp. 480-485.

Saijilafu, Hur E M, Liu C M, Jiao Z, Xu W N, Zhou F Q. PI3K-GSK3 signaling regulates mammalian axon regeneration by inducing the expression of Smad1. Nature Communication. 2013; 4:2690.

Schwab, M. E. and Bartholdi, D., "Degeneration and regeneration of axons in the lesioned spinal cord.", Physiol. Rev. 1996, 76, pp. 319-370.

Sengottuvel V, Fischer D. Facilitating axon regeneration in the injured CNS by microtubules stabilization. Commun Integr Biol. 2011; 4:391-3.

Stambolic, V., Suzuki, A., De la Pompa, J. L. et al. "Negative regulation of PKB/Akt-dependent cell survival by the tumor suppressor PTEN.", Cell, 1998, 95(1), pp. 29-39.

Sun, F., Park, K. K., et al. "Sustained axon regeneration induced by co-deletion of PTEN and SOCS3", Nature, 2012, 480(7377), pp. 372-375.

Takahashi, Y., Morales, F. C., Kreimann, E. L. and Georgescu, G. M. "PTEN tumor suppressor associates with NHERF proteins to attenuate PDGF receptor signaling", EMBO J., 2006, 25, pp. 910-920.

Takemura R, Okabe S, Umeyama T, Kanai Y, Cowan N J, Hirokawa N. Increased microtubule stability and alpha tubulin acetylation in cells transfected with microtubule-associated proteins MAP1B, MAP2 or tau. J Cell Sci. 1992; 103:953-964.

Vazquez, F., and Devreotes, P. "Regulation of PTEN function as a $PIP_3$ gatekeeper through membrane interaction.", Cell Cycle, 2006, 5, pp. 1523-1527.

Vazquez, F., Grossman, S. R., Takahashi, Y., Rokas, M. V., Nakamura, N. and Sellers, W. R. "Phosphorylation of the PTEN Tail Acts as an Inhibitory Switch by Preventing Its Recruitment into a Protein Complex", J. Biol. Chem., 2001, 276, pp 48627-48630.

Walker, S. M., Leslie, N. R., Perera, N. M., Batty, I. H., and Downes, C. P. "The tumour-suppressor function of PTEN requires an N-terminal lipid-binding motif.", Biochem. J., 2004, 379, pp. 301-307.

Witte H, Neukirchen D, Bradke F, Microtubule stabilization specifies initial neuronal polarization. J Cell Biol. 2008; 180:619-632.

Yiu, G. and He, Z. "Glial inhibition of CNS axon regeneration.", Nat. Rev. Neurosci., 2006, 7, pp. 617-627.

Zhang, S. and Yu, D. "PI(3)King Apart PTEN's Role in Cancer", Clin Cancer Res, 2010, 16, pp. 4325-4330.

All of the references cited herein are incorporated by reference in their entirety.

Those skilled in the art will recognize, or be able to ascertain using no more than routine experimentation, many equivalents to the specific embodiments of the invention specifically described herein.

What is claimed is:

1. A method of regenerating a nerve or attenuating degeneration of a nerve at a site of nerve injury comprising administering at or an area near an injured nerve, a nerve regenerating or nerve degeneration attenuating amount of phosphatase and tensin homolog (PTEN) lipid phosphatase inhibiting peptide of amino acid sequence of SEQ ID NOS:3 to 6.

2. The method according to claim 1, wherein the peptide comprises a PDZ domain binding motif.

3. The method according to claim 1, wherein the peptide further comprises a peptide transfer domain (PTD).

4. The method according to claim 1, wherein the nerve injury is in the central nervous system.

5. A peptide which inhibits phosphatase and tensin homolog (PTEN) lipid phosphatase activity, wherein the peptide is a PTEN peptide of amino acid sequence of SEQ ID NOS:3 to 6.

6. The peptide according to claim 5, wherein the peptide comprises a PDZ domain binding motif.

7. The peptide according to claim 5, wherein the peptide further comprises a peptide transfer domain (PTD).

8. A method of growing, proliferating or enhancing cell activity of a nerve cell comprising contacting the nerve cell with a phosphatase and tensin homolog (PTEN) lipid phosphatase inhibiting peptide of amino acid sequence of SEQ ID NOS:3 to 6.

9. The peptide according to claim 8, wherein the peptide comprises a PDZ domain binding motif.

10. The peptide according to claim 8, wherein the peptide further comprises a peptide transfer domain (PTD).

* * * * *

SEQUENCE LISTING

```
<160> NUMBER OF SEQ ID NOS: 12

<210> SEQ ID NO 1
<211> LENGTH: 403
<212> TYPE: PRT
<213> ORGANISM: Artificial Sequence
<220> FEATURE:
<223> OTHER INFORMATION: PTEN amino acid sequence

<400> SEQUENCE: 1

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60
```

```
Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
            115                 120                 125

Gly Arg Thr Gly Val Met Ile Cys Ala Tyr Leu Leu His Arg Gly Lys
            130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
                180                 185                 190

Leu Leu Phe His Lys Met Met Phe Glu Thr Ile Pro Met Phe Ser Gly
            195                 200                 205

Gly Thr Cys Asn Pro Gln Phe Val Val Cys Gln Leu Lys Val Lys Ile
            210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
            275                 280                 285

Lys Val Glu Asn Gly Ser Leu Cys Asp Gln Glu Ile Asp Ser Ile Cys
            290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
                340                 345                 350

Glu Pro Ser Asn Pro Glu Ala Ser Ser Thr Ser Val Thr Pro Asp
            355                 360                 365

Val Ser Asp Asn Glu Pro Asp His Tyr Arg Tyr Ser Asp Thr Thr Asp
            370                 375                 380

Ser Asp Pro Glu Asn Glu Pro Phe Asp Glu Asp Gln His Thr Gln Ile
385                 390                 395                 400

Thr Lys Val

<210> SEQ ID NO 2
<211> LENGTH: 8
<212> TYPE: PRT
<213> ORGANISM: Artificial Sequence
<220> FEATURE:
<223> OTHER INFORMATION: PTD (peptide transfer domain)

<400> SEQUENCE: 2

Arg Arg Arg Arg Arg Arg Arg
1               5
```

```
<210> SEQ ID NO 3
<211> LENGTH: 27
<212> TYPE: PRT
<213> ORGANISM: Artificial Sequence
<220> FEATURE:
<223> OTHER INFORMATION: TGN-1 peptide

<400> SEQUENCE: 3

Val Thr Pro Asp Val Pro Ser Asp Asn Glu Pro Asp His Tyr Arg Tyr
1               5                   10                  15

Pro Ser Asp Thr Thr Asp Pro Ser Asp Pro Glu
            20                  25

<210> SEQ ID NO 4
<211> LENGTH: 35
<212> TYPE: PRT
<213> ORGANISM: Artificial Sequence
<220> FEATURE:
<223> OTHER INFORMATION: PTD and TGN-1

<400> SEQUENCE: 4

Arg Arg Arg Arg Arg Arg Arg Arg Val Thr Pro Asp Val Pro Ser Asp
1               5                   10                  15

Asn Glu Pro Asp His Tyr Arg Tyr Pro Ser Asp Thr Thr Asp Pro Ser
            20                  25                  30

Asp Pro Glu
        35

<210> SEQ ID NO 5
<211> LENGTH: 30
<212> TYPE: PRT
<213> ORGANISM: Artificial Sequence
<220> FEATURE:
<223> OTHER INFORMATION: PTD and TGN-2

<400> SEQUENCE: 5

His Tyr Arg Tyr Pro Ser Asp Thr Thr Asp Pro Ser Asp Pro Glu Asn
1               5                   10                  15

Glu Pro Phe Asp Glu Asp Gln His Thr Gln Ile Thr Lys Val
            20                  25                  30

<210> SEQ ID NO 6
<211> LENGTH: 38
<212> TYPE: PRT
<213> ORGANISM: Artificial Sequence
<220> FEATURE:
<223> OTHER INFORMATION: PTD and TGN-2

<400> SEQUENCE: 6

Arg Arg Arg Arg Arg Arg Arg Arg His Tyr Arg Tyr Pro Ser Asp Thr
1               5                   10                  15

Thr Asp Pro Ser Asp Pro Glu Asn Glu Pro Phe Asp Glu Asp Gln His
            20                  25                  30

Thr Gln Ile Thr Lys Val
        35

<210> SEQ ID NO 7
<211> LENGTH: 28
<212> TYPE: PRT
<213> ORGANISM: Artificial Sequence
<220> FEATURE:
<223> OTHER INFORMATION: PTD and TGN-3

<400> SEQUENCE: 7
```

His Tyr Arg Tyr Val Asp Thr Thr Asp Val Asp Pro Glu Asn Glu Pro
1               5                   10                  15

Phe Asp Glu Asp Gln His Thr Gln Ile Thr Lys Val
                20                  25

<210> SEQ ID NO 8
<211> LENGTH: 36
<212> TYPE: PRT
<213> ORGANISM: Artificial Sequence
<220> FEATURE:
<223> OTHER INFORMATION: PTD and TGN-3

<400> SEQUENCE: 8

Arg Arg Arg Arg Arg Arg Arg Arg His Tyr Arg Tyr Val Asp Thr Thr
1               5                   10                  15

Asp Val Asp Pro Glu Asn Glu Pro Phe Asp Glu Asp Gln His Thr Gln
                20                  25                  30

Ile Thr Lys Val
        35

<210> SEQ ID NO 9
<211> LENGTH: 23
<212> TYPE: PRT
<213> ORGANISM: Artificial Sequence
<220> FEATURE:
<223> OTHER INFORMATION: PTD and TGN-4

<400> SEQUENCE: 9

Ser Asp Asp Glu Tyr Thr Asp Asn Pro Asp Ser Arg Tyr Val Ser Asp
1               5                   10                  15

Thr Pro Val Asp Thr Glu His
                20

<210> SEQ ID NO 10
<211> LENGTH: 31
<212> TYPE: PRT
<213> ORGANISM: Artificial Sequence
<220> FEATURE:
<223> OTHER INFORMATION: PTD and TGN-4

<400> SEQUENCE: 10

Arg Arg Arg Arg Arg Arg Arg Arg Ser Asp Asp Glu Tyr Thr Asp Asn
1               5                   10                  15

Pro Asp Ser Arg Tyr Val Ser Asp Thr Pro Val Asp Thr Glu His
                20                  25                  30

<210> SEQ ID NO 11
<211> LENGTH: 28
<212> TYPE: PRT
<213> ORGANISM: Artificial Sequence
<220> FEATURE:
<223> OTHER INFORMATION: PTD and TGN-5

<400> SEQUENCE: 11

Asp Glu His Asp Thr Glu Tyr Thr Pro Asp Tyr Arg Gln Glu Thr His
1               5                   10                  15

Phe Asn Ser Gln Pro Thr Asp Lys Ser Asp Val Ile
                20                  25

<210> SEQ ID NO 12
<211> LENGTH: 36
<212> TYPE: PRT
<213> ORGANISM: Artificial Sequence
<220> FEATURE:

-continued

<223> OTHER INFORMATION: PTD attached at the N-terminus of TGN-5

<400> SEQUENCE: 12

```
Arg Arg Arg Arg Arg Arg Arg Arg Asp Glu His Asp Thr Glu Tyr Thr
1               5                   10                  15
Pro Asp Tyr Arg Gln Glu Thr His Phe Asn Ser Gln Pro Thr Asp Lys
            20                  25                  30
Ser Asp Val Ile
        35
```